US006426370B1

(12) United States Patent
Hofschneider

(10) Patent No.: US 6,426,370 B1
(45) Date of Patent: *Jul. 30, 2002

(54) USE OF THIOL COMPOUNDS IN VIRAL INACTIVATION

(76) Inventor: Peter Hofschneider, Nördliche Auffahrtsallee 65, München (DE), D-80638

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/485,793

(22) PCT Filed: Aug. 12, 1998

(86) PCT No.: PCT/DE98/02370

§ 371 (c)(1),
(2), (4) Date: Apr. 19, 2000

(87) PCT Pub. No.: WO99/08665

PCT Pub. Date: Feb. 25, 1999

(51) Int. Cl.$^7$ ...................... A61K 31/095; A01N 31/00
(52) U.S. Cl. ........................ 514/706; 504/349
(58) Field of Search ............................ 514/706; 504/349

(56) References Cited

U.S. PATENT DOCUMENTS 4,534,972 A * 8/1985 Lembach ..................... 424/86

FOREIGN PATENT DOCUMENTS

| WO | WO 90/05135 A | 5/1990 |
| WO | WO 95/03792 A | 2/1995 |
| WO | WO 96/04242 A | 2/1996 |
| WO | WO 96/10402 A | 4/1996 |

OTHER PUBLICATIONS

Lioy et al, Thiol suppression of human immunodeficiency virus type 1 replication in primary cord blood monocyte–derived macrophages in vitro, J. Clin. Invest., 91(2); 495–498, 1993.*

Barnett and Fulton, 1971, "Differential Response of Prunus Necrotic Ringspot and Tulare Apple Mosaic Viruses to Stabilizing Agents," *Virology* 46(3):613–619.

Kameoka et al., 1996, "Intracellular glutathione as a possible direct blocker of HIV type 1 reverse transcription," *AIDS Res. Hum. Retroviruses*, 12(17):1635–1638.

Lioy et al., 1993, "Thiol suppression of human immunodeficiency virus type 1 replication in primary cord blood monocyte–derived macrophages in vitro," *J. Clin. Invest.* 91(2):495–498.

McDonnell et al., 1997, "Zinc ejection as a new rationale for the use of cystamine and related disulfide–containing antiviral agents in the treatment of AIDS," *J. Med. Chem.* 40(13):1969–1976.

Murata and Kitagawa, 1973, "Mechanism of inactivaiton of bacteriophase J1 by dithiothreitol, cysteine, mercaptoethanol, or thioglycollate," *Agr. Biol. Chem.* 37(9):2159–2165.

Olivier et al., 1994, "Prevention of early cell death in peripheral blood lymphocytes of HIV infected individuals by an anti-oxidant: N–acetyl–cysteine," *Oxidative Stress, Cell Activation Viral Infection* 323–332.

Roederer et al., 1990, "Cytokine–stimulated human immunodeficiency virus replication is inhibited by N–acetyl–L–cysteine," *Proc. Natl. Acad. Sci. U.S.A.* 87(12):4884–4888.

Sells et al., 1987, "Production of hepatitis B virus particles in Hep G2 cells transfected with cloned hepatitis B virus DNA," *Proc. Natl. Acad. Sci. U.S.A.* 84(4):1005–1009.

Shoji et al., 1994, "Thiamine disulfide as a potent inhibitor of human immunodeficiency virus (type–1) production," *Biochem. Biophys. Res. Commun.* 205(1):967–975.

Totsuka and Ohtaki, 1974, "The effects fo amino acids and metals on the infectivity of poliovirus ribonucleic acid," *Jpn. J. Microbiol.* 18(2):107–112.

* cited by examiner

*Primary Examiner*—Alton Pryor
(74) *Attorney, Agent, or Firm*—Pennie & Edmonds LLP

(57) ABSTRACT

The invention relates to the use of thiol compounds in viral inactivation in a cell-free environment, especially in the blood, blood plasma, blood serum, conserved blood, blood products, cell culture liquids and nutrient media and to the application of said compounds on the surface of plants and animals. Viral inactivation occurs without requiring cell metabolism.

10 Claims, 3 Drawing Sheets

USE OF THIOL COMPOUNDS IN VIRAL INACTIVATION

This is a national phase filing of the Application No. PCT/DE98/02370, which was filed with the Patent Corporation Treaty on Aug. 12, 1998, and is entitled to priority of the German Patent Application 197 35 120.4, filed Aug. 13, 1997.

FIELD OF THE INVENTION

The present invention relates to the use of thiol compounds for the inactivation of viruses in a cell-free environment, especially in the blood, blood plasma, blood serum, conserved blood, blood products, cell culture liquids and nutrient media and when applied onto the surface of plants and animals. In this connection, viral inactivation occurs without requiring cell metabolism.

BACKGROUND OF THE INVENTION

Methods of viral inactivation, which have been common by now, comprise the irradiation with radiation rich in energy, such as U.V. light and X-rays. In this case, the objective is to damage nucleic acid molecules in the viral genome to thereby reduce the information content of the viral genetic information. By preceding staining of the viral genome using dyes which can penetrate the viral envelope (e.g., neutral red or proflavines), the viral genome can already be influenced by visible light. The treatment of virus suspensions with formaldehyde, used in viral inactivation to obtain viral vaccines, also leads predominantly via a destruction of the viral genome to a reduction of the infectiosity of these viruses. Thus, said treatment methods influence substantially the genetic material of the virus, they do not influence the composition of the viral envelope and the capability of the virus to penetrate the host cell.

Methods which prevent the attachment of the virus to its host cell—i.e., the first step of the process of infection-require a modification of the viral coat proteins. Such methods are, e.g., the separation of the outer viral envelope of what is called "enveloped viruses" by the addition of ether or detergents such as Nonidet P40, Triton X100 or sodium dodecyl sulfate (SDS). Many disinfectants which are used successfully to combat bacteria, such as chlorine compounds, have no influence on the replication of viruses.

However, there are also chemical agents having both an antibacterial effect and an antiviral effect. For example, formalin and in certain viruses also alcohols (ethanol, isopropanol) have an antiviral effect at high concentrations. However, these compounds can only be used for the purpose of disinfection. Their use, e.g., for viral inactivation in blood and blood products is not possible, since these substances having a cytotoxic and denaturing effect also destroy the blood proteins and thus prohibit, or make impossible, a further use of the derived products and their application in patients. In addition, said substances are not suitable for viral inactivation on the surface of plants, since they would kill the plant.

An essential requirement for the inactivation of viruses which are located in the direct vicinity of living cells (e.g., on the leaves of planes) or which occur in liquids in contact with living cells, is represented by the fact that the virus-inactivating agent has no cytotoxic properties.

Therefore, it is the object of the present invention to provide agents for viral inactivation in liquids (particularly in the blood, blood plasma, blood serum and blood products, cell culture liquids, nutrient media) and on the surface of plants and animals, which distinguish themselves by a low cytotoxic and/or denaturing effect. In contrast to the use of radiation rich in energy, the target of the antiviral effect is not the viral nucleic acid but the influence of viral surface proteins to already prevent the virus from entering into the host cell.

SUMMARY OF THE INVENTION

The invention relates to the use of thiol compounds in viral inactivation in a cell-free environment, especially in the blood, blood plasma, blood serum, conserved blood, blood products, cell culture liquids and nutrient media and to the application of said compounds on the surface of plants and animals. Viral inactivation occurs without requiring cell metabolism.

DETAILED DESCRIPTION OF THE INVENTION

Figure 1:
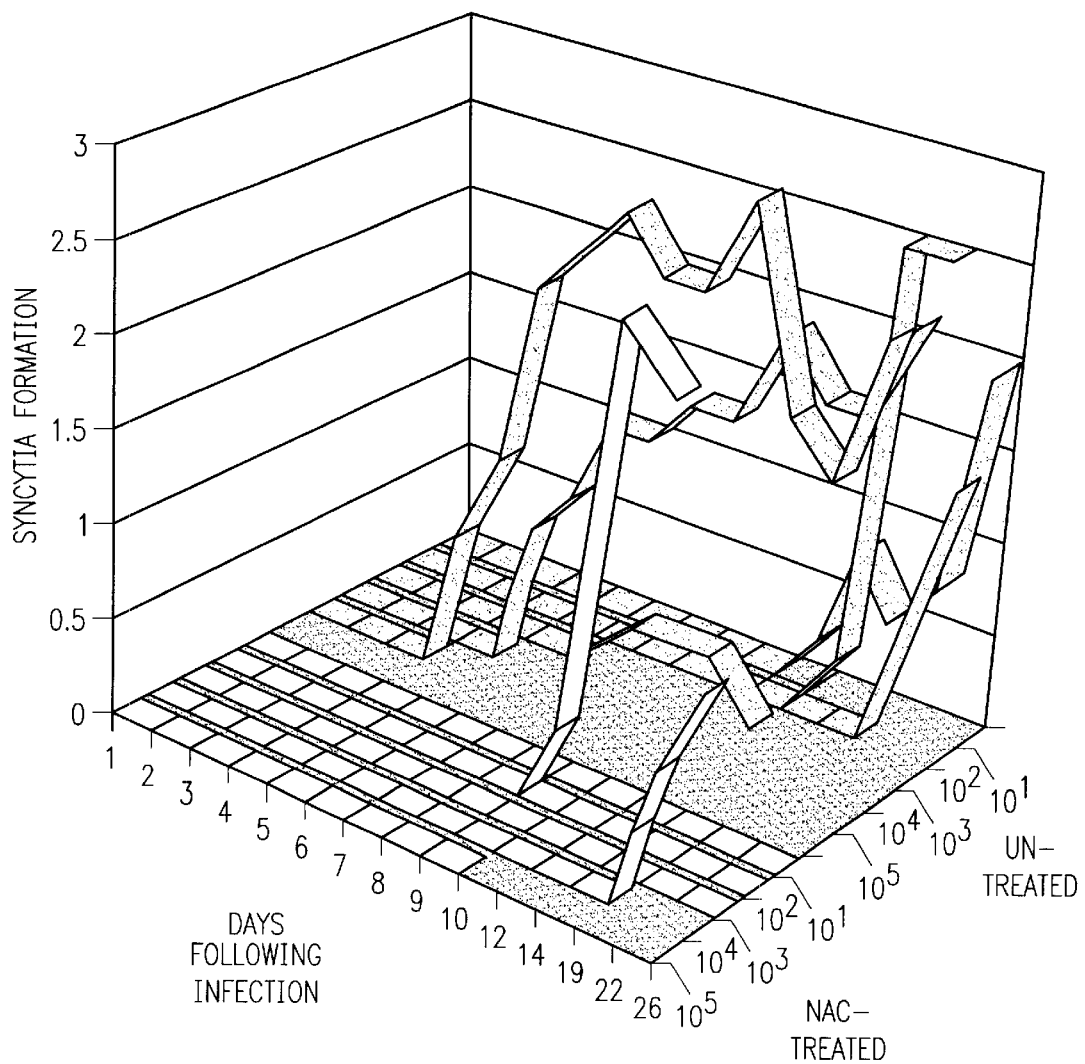
FIG. 1 shows the syncytia formation of HIV-infected H9 cells after pre-incubation of the virions with NAC.

It is the object of the present invention to provide agents for viral inactivation in liquids (particularly in the blood, blood plasma, blood serum and blood products, cell culture liquids, nutrient media) and on the surface of plants and animals, which distinguish themselves by a low cytotoxic and/or denaturing effect. In contrast to the use of radiation rich in energy, the target of the antiviral effect is not the viral nucleic acid but the influence of viral surface proteins to already prevent the virus from entering into the host cell. The object of the invention is achieved by the subject matters defined in the claims.

In particular, this object is achieved by using thiol compounds for the inactivation of viruses. This invention differs from the treatment of viral diseases in that the assistance of the metabolic apparatus of the host cell is surprisingly not necessary for viral inactivation. The present invention does not serve the treatment of viral diseases, i.e., the prevention of virus replication in a living organism, but the inactivation of already existing viruses outside the living organism. Thus, it can also be carried out in cell-free environments (e.g., in liquids or on the surface of plants and animals). In this connection, the successful use of thiol compounds is based on the destruction of disulfide bridges in viral proteins.

The expression "thiol compound" is understood to mean chemical compounds which are characterized by the presence of a reduced thiol group (SH group). Preferred examples of such thiol compounds are cysteine, cysteine derivatives, mercaptoalkanols, such as methanethiol, ethanethiol or mercaptoethanol, dithiocarbamate, thiophenol and 2-mercaptoethane sulfonic acid. Examples according to the invention of cysteine derivatives are N-acetyl cysteine, N-acetyl cysteine derivatives, such as N-acetyl homocysteine, N-acetyl cysteine ethyl ester or N,S-diacetylcysteine ethyl ester. N-acetyl cysteine (NAC) and its derivatives are particularly preferred.

The thiol compounds used according to the invention are also characterized by their non-toxicity within the usually employed concentration range. This adds to their safety for use in viral inactivation in blood, nutrient media, cell culture liquids and blood products as well as their application in natural environments, e.g., when plants are sprayed and animals are bathed with dissolved thiol compounds, respectively.

The expression "disulfide bridges in viral proteins" refers to disulfide bridges which influence the three-dimensional structure and function of viral proteins by intramolecular or intermolecular covalent bonds. Correspondingly, the viral proteins, but at least one viral protein, contains at least one cysteine residue. The viral protein preferably contains several cysteine residues, such as the surface proteins of the hepatitis B virus (HBsAg) or the human immunodeficiency virus (gp120). It is known that disulfide bridges are stabilized by the conformation of the protein. Therefore, the amount of thiol compound to be used, which is necessary to separate the already existing intramolecular or intermolecular disulfide bridge(s), depends on the accessibility of the respective disulfide bridge(s). In this connection, concentrations of up to 100 mM, particularly 1–100 mM, of thiol compound, have proved their worth in the viral inactivation in the blood, blood plasma, blood serum, conserved blood, blood products, cell culture liquids and nutrient media, particularly in the case of N-acetyl cysteine. In this case, the addition can be made by admixing the solid to the liquid or by inserting an aqueous dilution up to the desired concentration.

For the application onto plants, seeds, sprouts, and seedlings or saplings by means of spraying, immersion, washing or germination concentrations of up to 100 mM of thiol compound suffice, particularly in the case of N-acetyl cysteine. Equal concentrations can also be used for the external treatment of domestic and useful animals. This can be done by rubbing in or rubbing off or bathing the animals in an aqueous dilution of the thiol compound.

The plants are ornamental and useful plants, e.g., grain (oat, rye, barley, corn, wheat, soybean, rice, millet, couscous), vegetables (pod vegetables, root vegetables, cabbage varieties, leek, potatoes), fruit (apples, pears, lemons, oranges), trees (e.g., citrus fruit trees), foliage and flowering plants as well as further monocotyl and dicotyl plants. Plants are also understood to mean hydroponics and vegetable tissue and cell cultures.

The viruses to be mentioned are, e.g., DNA viruses, such as hepadnaviridae, parvoviridae, papovaviridae, adenoviridae, herpesviridae, poxviridae, iridoviridae, or PEA viruses, such as picomaviridae, caliciviridae, togaviridae, flaviviridae, paramyxoviridae, orthomyxoviridae, bunyaviridae, arenaviridae, reoviridae, bimaviridae, and RNA retroviruses, such as HIV.

Plant-pathogenic viruses are, e.g., tobacco mosaic virus, cauliflower mosaic virus, bromomosaic virus, rice necrosis virus or gemini virus.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

EXAMPLES

Example 1

Reduction of the Infectiosity of the Human Immunodeficiency Virus (Lily) by N-Acetyl Cysteine (NAC)

In order to examine whether NAC influences the HIV infection of cells, HIV-permissive cells (119 cells) were incubated together with HIV-positive cell culture supernatant and the syncytia formation taking place upon successful infection of the host cell was observed. The H9 cell line is a CD4+ T-cell line of human origin (Popovic et al., 1984, *Science* 224:497–500). The HI virions (viral titer of the original solution is $10^7$ viruses/ml) were initially pre-incubated together with NAC at room temperature for two hours (final NAC concentration 0.09 M, dissolved in serum-free cell culture medium) and then mixed with cell culture medium in a decadic dilution series ($10^{-1}$ to $10^{-5}$). The same was made analogously with the control without NAC addition. Thereafter, the thus pretreated virions (and the untreated control, respectively) were added to the H9 cell culture for two hours to enable the adsorption of the viruses. Then, the suspension was washed with NAC-free medium and 48-well cell culture plates were covered therewith. Pour parallel assays were carried out for each dilution series. The giant cell formation was observed microscopically over an observation period of 26 days and assessed on a scale from 0 (no syncytia detectable) to 3 (great number of syncytia). The result of syncytia formation is shown in FIG. 1 by way of diagram. It can be seen in connection with the untreated control (FIG. 1) that the syncytia formation is delayed when the viral titer decreases. The degree of syncytia formation is thus directly proportional to the number of infectious viruses. While with a viral titer of $10^5$ the syncytia formation starts within four days already, it is delayed by about 2 weeks when the original virus solution has been diluted 10,000 times. In contrast thereto, the infectious viruses in the original virus solution are drastically reduced after pretreating the viruses with NAC. If the NAC-treated virions were diluted by more than 100 times (viral titer $<10^4$), it was no longer possible to observe syncytia formation within the observation period of four weeks at all, whereas the first giant cells had formed in the untreated control under comparable conditions after one week already.

Thus, an initial treatment of the viruses with NAC resulted in a drastic reduction of the content of infectious viruses in a virus-containing liquid. The experiment described herein differs clearly from the treatment of HIV-infected cells with NAC. When cells are treated with NAC, NAC interferes with the cellular metabolism as an oxygen radical trap and reduces in this way the number of viral PEA replication intermediates which are packaged into the nucleocapsid (Roederer et al., 1990, *Proc. Natl. Acad. Sci. U.S.A.* 87: 4884–4888). However, in the above described experimental assay the viruses were pre-incubated with NAC in the absence of cells and added to the cell suspension only afterwards, i.e., after the removal of NAC by dilution. Therefore, the decrease in infectiosity must have been due to a destruction of the virions in the cell-free original virus solution and cannot have been caused by the influence of the cellular metabolism. As a result, it follows from the data shown that the infectiosity of HIV-positive blood or HIV-positive blood products can also be reduced by analogous steps, which adds to the safety of conserved blood.

The delay of giant cell formation, which is shown in FIG. 1, is due to a reduction of the number of infectious virions— because of a correlation between viral titer and the number of syncytia. It is in no case caused by an influence of the metabolism of the host cell. The reduced capability to form giant cells (FIG. 1) can be quantified as titer exponent n by observing the laws established by Spearmann-Kärber.

| Class limit       | −5    | −4    | −3    | −2    | −1  |
|-------------------|-------|-------|-------|-------|-----|
| Test positives p/4 | 0/4   | 2/4   | 1/4   | 1/4   | 4/4 |
| Class midpoint m  | −4, 5 | −3, 5 | −2, 5 | −1, 5 |     |
| Increase Δp       | 2     | −1    | 0     | 3     |     |
| Product m*Δp      | −9    | 3, 5  | 0     | −4, 5 |     |

With a total number of 4 preparations per dilution series there is $$n = \frac{\sum m \cdot \Delta p}{4}.$$

Thus, nNAC=−2.5 follows for the titer exponent after NAC treatment. Since the dilution stage of the untreated control, where syncytia formation could no longer be observed, was not determined accurately in this experiment, the maximum value for this preparation, i.e., $10^{-6}$ was assumed as a calculation basis. Correspondingly, the titer of the untreated control is $10^{-5,5}$ or less. The titer after the NAC treatment is $10^{-2,5}$. Measured on the basis of the syncytia formation capability, the NAC treatment resulted in a reduction of the viral titer by at least three decimal exponents.

This reduction of the infectiosity titer could also be confirmed by means of the p24-Ag test. For this purpose, the cell culture medium was renewed four days prior to the end of the experiment and the p24-Ag content of the cell culture medium was quantified upon termination of the experiment (day 26) (TABLE I). The p24-Ag values of the untreated control were always clearly positive. As compared thereto, the NAC treatment carried out prior to the infection caused a marked reduction of the p24-Ag content in the cell culture medium from an HIV dilution factor of 1/100 on, which is equal with a reduction in the number of infectious virions and thus also a reduction of the viral titer (TABLE 1).

TABLE I

The P24-Ag Content in the Cell Culture Medium of HIV-infected H9 Cells Is Reduced If the Virions Are Treated with NAC Prior to the Infection

| Dilution | NAC-treated | | | | untreated | | | |
|----------|------|------|------|------|------|------|------|------|
| $10^{-1}$ | >2.0 | >2.0 | >2.0 | >2.0 | >2.0 | >2.0 | >2.0 | >2.0 |
| $10^{-2}$ | 0.045 | 0.038 | >2, 0 | 0.079 | >2.0 | >2.0 | >2.0 | >2.0 |
| $10^{-3}$ | 0.044 | 0.047 | 0.039 | 0.274 | >2.0 | >2.0 | >2.0 | >2.0 |
| $10^{-4}$ | 0.047 | 0.044 | 0.134 | 0.652 | >2.0 | >2.0 | 1.512 | >2.0 |
| $10^{-5}$ | 0.069 | 0.04 | 0.044 | 0.04 | 0.238 | >2.0 | >2.0 | >2.0 |

The p24-Ag detection was made 26 days after the infection in the cell culture meduim of HIV-infected H9 cells. The extinction is given at 492 nut in the table. (Exclusion limit O.D. 492 nm; <0.093; the extinction of the non-infected control was 0.4040; titer of the original virus solution: $10^6$).

The difference between the experiment herein and the experimental preparations published many times already consists in that the virions had been treated with NAC prior to the infection of the H9 cells, i.e., in the absence of the cells, and were added to the cells only afterwards. According to the current state of the art it is common practice to permanently treat HIV-infected cells with NAC. Correspondingly, the cause of the anti-HIV effect of NAC must be due to the effect of NAC as a radical trap, which leads to the known proposal of using NAC for the treatment of HIV infections.

The here presented reduction of the viral titer by at least three decimal exponents and the reduction of the p24-Ag content even after 26 days following initial infection of the cells, without the cells per se having been exposed to NAC, rule out a radical trap effect of NAC as a cause of the antiviral effect of NAC. The antiviral effect can rather be explained by a disturbance of the virus adsorption, by the separation of disulfide bridges between conserved cysteine residues in the coat protein gp120 of HIV. Such a mechanism is independent of the infected cell and is therefore no treatment of a viral infection. It is rather the chemical inactivation of a virus.

Example 2

Treatment of the Hepatitis B Virus (HBV) Surface Protein HBsAg with N-Acetyl Cysteine (NAC)

Figure 2:
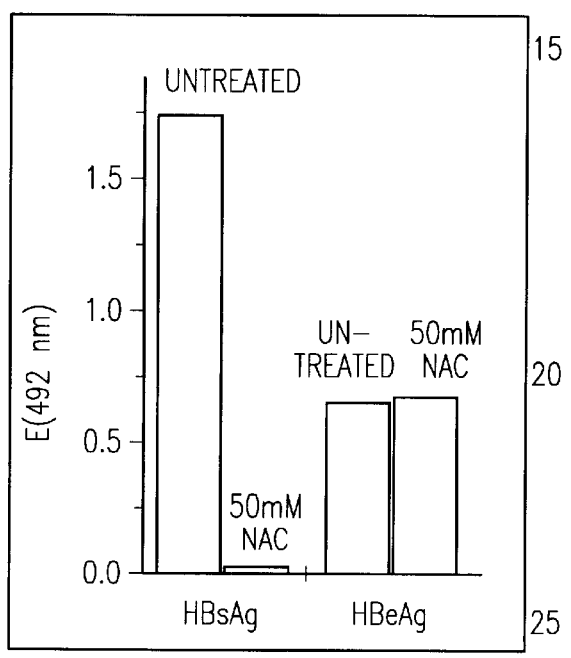
FIG. 2 shows an EIA test of untreated HBsAg with 50 mM NAC-treated HBsAg, untreated HBsAg and with 50 mM NAC-treated HBeAg.

The cell culture supernatant of a HBV-producing cell line (HepG2–2.2.15 cells, Sells et al., 1984, Proc. Natl. Acad. U.S.A. 84:1005–1009) was separated from the cells and then the viral antigens (HBsAg, hepatitis-B virus "surface" antigen) of the viral envelope were identified by means of an enzyme immunoassay (EIA). In a parallel experimental assay, the cell culture supernatant was treated with NAC directly before the EIA was carried out. While the HBeAg (hepatitis-B virus "e" antigen; secretable viral antigen which is not part of the viral envelope) was recognized unrestrictedly also in the presence of 50 mM NAC by the test system employed (Abbott HBe EIA), detection of the HBsAg was not possible by the test system (Abbott Auszyme*) (FIG. 2). Since as is known the main antigenic domain of HBsAg is stabilized by numerous disulfide bridges, it can be inferred from this experiment that NAC effects a change in the three-dimensional structure on the virus surface, which is caused by a separation of disulfide bridges. These very viral surface structures are essential for the attachment of the virus to its host cell and thus for its infectiosity.

Example 3

Reduction of the Infectiosity of Vaccinia Viruses by NAC

Figure 3:
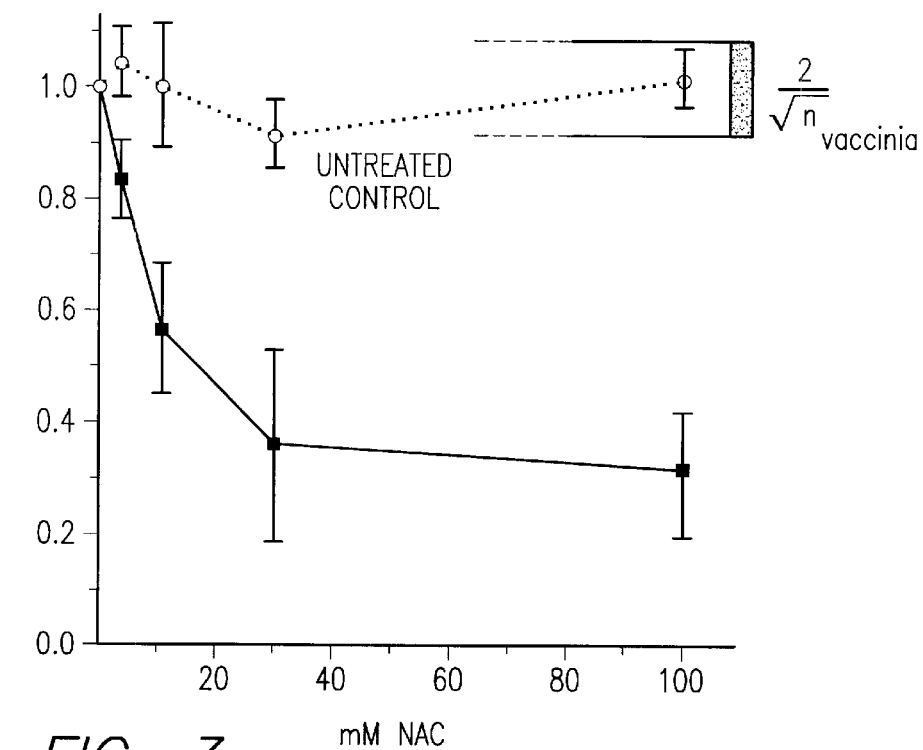
FIG. 3 shows a reduction of the infectiosity of vaccinia viruses following NAC treatment.
Figure 4:
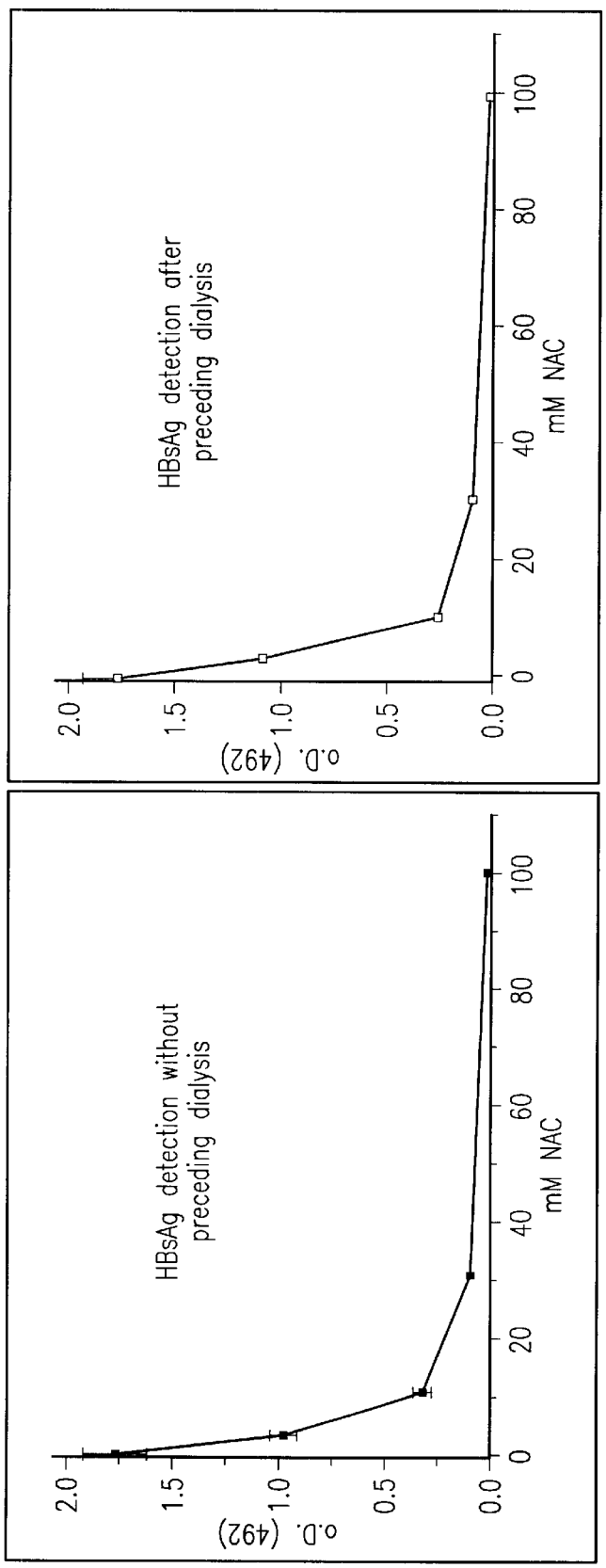
FIG. 4 shows removal of excess NAC by dialysis.

In order to find out whether NAC has an influence on the infectiosity of vaccinia viruses, an original vaccinia virus solution was pre-incubated with increasing amounts of NAC (3, 10, 30 mM) and then an infection of permissive cells (CV1 cells, monkey kidney cells) was carried out. Following the removal of the non-adsorbed viruses, the cells were coated with soft agar medium to prevent further spreading of the viruses by diffusion. In this connection, it could be shown that the viral titer of the vaccinia virus suspension was reduced by up to 70% (FIG. 3). This reduction of the infectiosity was markedly above the range of variations of the plaque assay (Akkuranz) which was calculated on the basis of the number of plaques of the untreated sample and was ±9%. As shown similarly for HBV and HIV already, NAC also effects a reduction of the infectiosity of vaccinia viruses.

Therefore, it could be shown for three different viruses (HIV, HBV and vaccinia) which belong to three completely different classes of virus (retroviruses (RNA genome), hepadnaviruses (DNA genome) and pox viruses (DNA genome)) that thiol compounds (particularly NAC) effect a reduction of the infectiosity of these viruses.

Example 4

Method of Removing NAC from Liquids after Viral Inactivation

Hence the addition of NAC to virus-containing liquids effects a decrease in the infectiosity of the liquid (shown for HIV, HBV and vaccinia viruses). Therefore, the use of thiol derivatives (such as NAC) results in an inactivation of viruses particularly in the blood, conserved blood, blood plasma, blood serum and blood preparations. In this connection, it may be advantageous to remove the thiol derivatives used in viral inactivation after inactivation of the viruses again. In order to examine which influence the removal of NAC from virus-containing suspensions has on the infectiosity of the viruses, HBV-positive cell culture supernatant was initially incubated with different amounts of NAC in two parallel assays for 15 minutes. To remove the unbound NAC again, one assay was dialyzed against TNE buffer (10 mM Tris-HCl, pH 7.5; 100 mM NaCl; 1 mM EDTA) at 4° C. overnight, whereas the other assay remained untreated.

Irrespective of whether or not the sample was dialyzed overnight, the same curve was obtained in either case (FIG. 4). This shows that excess amounts of NAC can be removed by dialysis again without the antigenicity and thus infectiosity of the virus suspension increasing again. Therefore, it can be recorded that the effect which NAC exerts on the viruses is irreversible and that dialysis is a suitable method of removing excess NAC. The result of FIG. 4 also shows that NAC enters into chemical bonding with HBsAg. Otherwise the effect could be reversed by dialysis. Therefore, the inactivation of viruses by NAC is a chemical reaction which takes place between the free SH group of the thiol compound and a disulfide bridge in the viral protein. The presence of a cellular metabolic apparatus is not necessary for this purpose.

Examples 5

Viral Inactivation by N-Acetyl Cysteine on Plants

In addition to the wide applicability of thiol derivatives for viral inactivation in liquids, inactivation of viruses in their natural environment is also possible.

Since as is known NAC shows no cytotoxic effects, it can also be used as an extremely environmentally compatible and simultaneously biodegradable preparation for combating plant-pathogenic viruses. It is assessed that losses amounting to about 60 billion US $ are caused by plant viruses each year. Very often, plant viruses are transmitted mechanically. The viruses can be further spread inter alia by direct contact of the infected plant with a neighboring plant, by transmission of the viruses by means of insects, spores, etc., or via already infected seeds. Irrespective of the kind of transmission, spraying or immersion of the host plant (e.g., the seeds) with thiol compounds (e.g., NAC) has a prophylactic effect, since the viruses are already inactivated on the plant surface in this way and can no longer penetrate the interior of the host cell. Thiol compounds can thus make a valuable contribution to viral inactivation in agriculture as well.

All references cited within the body of the instant specification are hereby incorporated by reference in their entirety.

What is claimed is:

1. A method for inactivating viruses in a cell-free environment, comprising treating said cell-free environment with an effective amount of a composition consisting essentially of thiol compound.

2. The method of claim 1, wherein said cell-free environment is a cell-free liquid.

3. The method of claim 1, wherein said cell-free liquid is blood, conserved blood, blood plasma, blood serum, blood preparations, cell culture liquids, or nutrient media.

4. The method of claim 1, 2, or 3, wherein said effective amount of said composition consisting essentially of thiol compound is in a concentration of 100 mM or less.

5. A method for inactivating viruses on the surface of plants or animals, comprising treating said surface of plants and animals with an effective amount of a composition consisting essentially of a thiol compound.

6. The method of claim 5, wherein the composition consisting essentially of thiol compound is applied to achieve a surface concentration of 100 mM or less.

7. The method of claim 1, 2, 3, 5, or 6, wherein said thiol compound is cysteine, a mercaptoalkanol, a dithiocarbamate, a thiophenol, or a 2-mercaptoethane sulfonic acid.

8. The method of claim 1, 2, 3, 5, or 6, wherein said thiol compound is an N-acetyl cysteine, an N-acetyl homocysteine, an N-acetyl cysteine ethyl ester, or an N,S-diacetyl cysteine ethyl ester.

9. The method of claim 7, where in said mercaptoalkanol is methanethiol, ethanethiol, or mercaptoethanol.

10. The method of claim 4 wherein said thiol compound is an N-acetyl cysteine, an N-acetyl homocysteine, an N-acetyl cysteine ethyl ester, or an N,S-diacetyl cysteine ethyl ester.

* * * * *